United States Patent [19]

Schohe-Loop et al.

[11] Patent Number: 5,403,849
[45] Date of Patent: Apr. 4, 1995

[54] 4-HETEROCYCLOPHENYL-SUBSTITUTED DIHYDROPYRIDINES

[75] Inventors: Rudolf Schohe-Loop; Wolfgang Hartwig; Bodo Junge; Heinrich Meier, all of Wuppertal, Germany; Zhan Gao, Beijing, China; Bernard Schmidt, Lindlar, Germany; Maarten de Jonge, Overath, Germany; Teunis Schuurman, Lohmar, Germany

[73] Assignee: Bayer Aktiengesellschaft, Leverkusen, Germany

[21] Appl. No.: 141,837

[22] Filed: Oct. 22, 1993

[30] Foreign Application Priority Data

Oct. 30, 1992 [DE] Germany ............... 42 36 706.9
Oct. 30, 1992 [DE] Germany ............... 42 36 705.0

[51] Int. Cl.⁶ ............... C07D 401/10; A61K 31/44
[52] U.S. Cl. ............... 514/340; 546/277; 546/281; 514/343
[58] Field of Search ............... 546/277; 514/340

[56] References Cited

U.S. PATENT DOCUMENTS

| | | | |
|---|---|---|---|
| 3,488,359 | 1/1970 | Bossert et al. | 546/321 |
| 3,574,843 | 4/1971 | Bossert et al. | 546/256 |
| 4,406,906 | 9/1983 | Meyer et al. | 514/356 |
| 4,510,310 | 4/1985 | Wehinger et al. | 546/321 |
| 4,568,681 | 2/1986 | Wehinger et al. | 546/321 |
| 4,590,276 | 5/1986 | King | 546/75 |
| 4,622,332 | 11/1986 | Wehinger et al. | 546/321 |
| 4,727,066 | 2/1988 | Sunkel et al. | 546/321 |
| 4,849,433 | 7/1989 | Wehinger et al. | 546/321 |
| 4,988,717 | 1/1991 | Wehinger et al. | 546/321 |

FOREIGN PATENT DOCUMENTS

| | | |
|---|---|---|
| 0373645 | 6/1990 | European Pat. Off. . |
| 0525568 | 2/1993 | European Pat. Off. . |
| 3816361 | 12/1988 | Germany . |

OTHER PUBLICATIONS

*Abstract*, 88-283059/40, B03, Fuji Oct. 9, 1986, JP-239353 (Aug. 30, 1988), "Optically Active 1,4-Dihydro:Pyridine Derivatives ..."; one page.
*TIPS*, vol. 111, Aug. 1990; I. Izquierdo, "Nimodipine and the Recovery of Memory"; 2 pages.
*Can. J. Physiol. Pharmacol.*, vol. 65, 1987, pp. 1452-1460; D. Rampe et al., "Comparative Aspects and Temperature Dependence of ...".

*Primary Examiner*—Jane T. Fan
*Attorney, Agent, or Firm*—Sprung Horn Kramer & Woods

[57] ABSTRACT

4-Heterocyclophenyl-substituted dihydropyridines

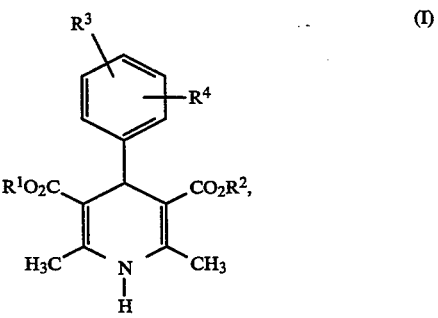

are prepared either by reacting suitable aldehydes with amino esters and β-keto esters, or preparing the heterocyclic substituents of the 4-phenyl by cyclization of corresponding amidines or hydrazides, or esterifying dihydropyridinecarboxylic acids, which are already substituted by heterocyclic radicals, with corresponding alcohols. The 4-heterocyclophenyl-substituted dihydropyridines can be employed in medicaments, in particular for treatment of diseases of the central nervous system.

8 Claims, No Drawings

4-HETEROCYCLOPHENYL-SUBSTITUTED DIHYDROPYRIDINES

The present invention relates to 4-heterocyclophenyl-substituted dihydropyridines, processes for their preparation and their use in medicaments, in particular as agents for treatment of diseases of the central nervous system.

The compound nimodipine and its cerebral activity are known [compare DOS 28 15 578]. 4-Heterocyclophenyl-substituted dihydropyridines having an antihypertensive action furthermore are known [compare JP 239 353; DE 38 16 361-A; EP 88 276 A; DE 32 39 273-A; DE 29 35 451; WO 84/02 132-A; NE 68 038 17; US 3 488 359; and US 3 574 843].

The present invention now relates to 4-heterocyclophenyl-substituted dihydropyridines of the general formula (I)

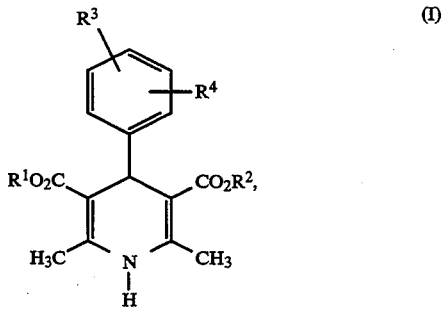

in which
$R^1$ and $R^2$ are identical or different and represent cycloalkyl having 3 to 8 carbon atoms, or represent straight-chain or branched alkyl having up to 8 carbon atoms, which is optionally substituted by straight-chain or branched alkoxy having up to 6 carbon atoms, cyano, cycloalkyl having 3 to 8 carbon atoms or aryloxy having 6 to 10 carbon atoms, which can in turn be mono-, di- or trisubstituted by identical or different substituents from the group comprising halogen, cyano and straight-chain or branched alkyl or alkoxy having up to 6 carbon atoms,
$R^3$ represents hydrogen, halogen, trifluoromethyl or cyano,
and
$R^4$ represents a 5-membered unsaturated heterocyclic radical having up to 4 hetero atoms from the series comprising N and/or O, which is bonded via a ring carbon atom and is optionally substituted by hydroxyl, straight-chain or branched alkyl or alkoxycarbonyl having in each case up to 6 carbon atoms, trifluoromethyl, halogen, carboxyl or a group of the formula —$NR^5R^6$, or
r $^4$ denotes a radical of the formula

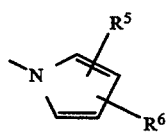

wherein $R^5$ and $R^6$ are identical or different and denote hydrogen or straight-chain or branched alkyl or alkoxycarbonyl having in each case up to 4 carbon atoms,
and salts thereof,
with the proviso that if $R^1$ and $R^2$ represent ethyl and $R^3$ represents hydrogen, $R^4$ may not denote the radical of the
formula

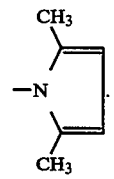

Physiologically acceptable salts of the compounds according to the invention are preferred.

Physiologically acceptable salts are in general salts of the compounds according to the invention with inorganic or organic acids. Preferred salts are those with inorganic acids, such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid, benzoic acid or methanesulphonic acid, ethanesulphonic acid, phenylsulphonic acid, toluenesulphonic acid or naphthalenedisulphonic acid.

The compounds according to the invention exist in stereoisomeric forms which either behave as image and mirror image (enantiomers) or do not behave as image and mirror image (diastereomers). The invention relates both to the antipodes and to the racemic forms, as well as to the diastereomer mixtures. The racemic forms, like the diastereomers, can be separated into the stereoisomerically uniform constituents in a known manner (compare E. L. Eliel, Stereochemistry of Carbon Compounds, McGraw Hill, 1962).

A 5-membered unsaturated heterocyclic radical having up to 4 hetero atoms from the series comprising N and/or O is in general imidazolyl, pyrrolyl, pyrazolyl, isoxazolyl, furyl, tetrazolyl, oxazolyl, 1,2,4- and 1,3,4-oxadiazolyl or 1,2,3-triazolyl. Tetrazolyl, 1,2,4-oxadiazolyl and 1,3,4-oxadiazolyl are preferred.

Preferred compounds of the general formula (I) are those
in which
$R^1$ and $R^2$ are identical or different and represent cyclopropyl, cyclopentyl, cyclohexyl or cycloheptyl, or represent straight-chain or branched alkyl having up to 6 carbon atoms, which is optionally substituted by straight-chain or branched alkoxy having up to 4 carbon atoms, cyano, cyclopropyl, cyclopentyl, cyclohexyl, cycloheptyl or phenoxy, which can in turn be mono-, di- or trisubstituted by identical or different substituents from the group comprising fluorine, cyano and straight-chain or branched alkyl or alkoxy having in each case up to 4 carbon atoms,
$R^3$ represents hydrogen, fluorine, chlorine, bromine, trifluoromethyl or cyano,
and
$R^4$ represents a tetrazolyl, 1,2,4-oxadiazolyl or 1,3,4-oxadiazolyl radical which is bonded via a ring carbon atom and is optionally substituted by hydroxyl, straight-chain or branched alkyl or alkoxycarbonyl having in each case up to 4 carbon atoms, trifluoromethyl, fluorine, chlorine or a group of the formula —NR$^5$R$^6$, or R$^4$ denotes a radical of the formula

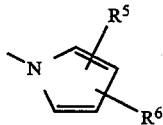

wherein

R$^5$ and R$^6$ are identical or different and denote hydrogen or straight-chain or branched alkyl or alkoxycarbonyl having in each case up to 3 carbon atoms, and salts thereof, with the proviso that if R$^1$ and R$^2$ represent ethyl and R$^3$ represents hydrogen, R$^4$ may not denote the radical of the formula

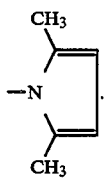

Particularly preferred compounds of the general formula (I) are those in which

R$^1$ and R$^2$ are identical or different and represent cyclopentyl, cyclohexyl or cycloheptyl, or represent straight-chain or branched alkyl having up to 4 carbon atoms, which is optionally substituted by methoxy, propoxy, cyclopentyl, cyclohexyl or cycloheptyl, R$^3$ represents hydrogen, chlorine, trifluoromethyl or cyano, and R$^4$ represents a tetrazolyl, 1,2,4-oxadiazolyl or 1,3,4-oxadiazolyl radical which is bonded via a ring carbon atom and is optionally substituted by straight-chain or branched alkyl or alkoxycarbonyl having in each case up to 3 carbon atoms, trifluoromethyl, fluorine, chlorine or amino, or R$^4$ denotes a radical of the formula

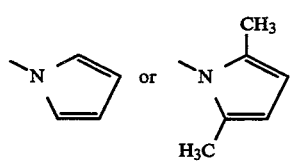

and salts thereof, with the proviso that if R$^1$ and R$^2$ represent ethyl and R$^3$ represents hydrogen, R$^4$ may not denote the radical of the formula

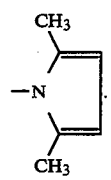

Especially preferred compounds of the general formula (I) are the following compounds in which R$^4$ represents a tetrazolyl, 1,2,4-oxadiazolyl or 1,3,4-oxadiazolyl radical bonded via a ring carbon:

Isopropyl 2-methoxyethyl 1,4-dihydro-2,6-dimethyl-4-[3-(1,2,4-oxadiazol-3-yl)phenyl]-pyridine-3,5-dicarboxylate Isopropyl 2-methoxyethyl 4-[3-(5-ethoxycarbonyl-1,2,4-oxadiazol-3-yl)-phenyl]-1,4-dihydro-2,6-dimethyl-pyridine-3,5-dicarboxylate Isopropyl 2-methoxyethyl (+)-4-[3-(5-ethoxycarbonyl-1,2,4-oxadiazol-3-yl)-phenyl]-1,4-dihydro-2,6-dimethyl-pyridine-3,5-dicarboxylate Isopropyl 2-methoxyethyl (−)-4-[3-(5-ethoxycarbonyl-1,2,4-oxadiazol-3-yl)-phenyl]-1,4-dihydro-2,6-dimethyl-pyridine-3,5-dicarboxylate Isopropyl 2-methoxyethyl 1,4-dihydro-2,6-dimethyl-4-[3-(tetrazol-5-yl)phenyl]-pyridine-3,5-dicarboxylate Isopropyl 2-methoxyethyl 1,4-dihydro-2,6-dimethyl-4-[3-(1,3,4-oxadiazol-2-yl)-phenyl]pyridine-3,5-dicarboxylate Isopropyl 2-methoxyethyl (+)-1,4-dihydro-2,6-dimethyl-4-[3-(2-methyl-1,3,4-oxadiazol-5-yl)-phenyl]pyridine-3,5-dicarboxylate Isopropyl 2-methoxyethyl (−)-1,4-dihydro-2,6-dimethyl-4-[3-(2-methyl-1,3,4-oxadiazol-5-yl)-phenyl]pyridine-3,5-dicarboxylate Isopropyl 2-methoxyethyl (−)-1,4-dihydro-2,6-dimethyl-4-[3-(1,3,4-oxadiazol-2-yl)-phenyl]pyridine-3,5-dicarboxylate Isopropyl 2-methoxyethyl (+)-1,4-dihydro-2,6-dimethyl-4-[3-(1,3,4-oxadiazol-2-yl)-phenyl]pyridine-3,5-dicarboxylate Isopropyl 2-propoxyethyl 1,4-dihydro-2,6-dimethyl-4-[3-(1,3,4-oxadiazol-2-yl)phenyl]-pyridine-3,5-dicarboxylate.

Especially preferred compounds of the general formula (I) are likewise the following compounds in which R$^4$ represents pyrrole or 2,5-dimethylpyrrole bonded via the nitrogen atom:

Isopropyl 2-methoxyethyl 1,4-dihydro-2,6-dimethyl-4-[3-(pyrrol-1-yl)phenyl]-pyridine-3,5-dicarboxylate Isopropyl-2-methoxyethyl 1,4-dihydro-2,6-dimethyl-4-[3-(2,5-dimethyl-pyrrol-1-yl)phenyl]-pyridine-3,5-dicarboxylate, Isopropyl 2-methoxyethyl 4-[2-chloro-3-(pyrrol-1-yl)phenyl]-1,4-dihydro-2,6-dimethyl-pyridine-3,5-dicarboxylate Isopropyl 2-methoxyethyl (+)-4-[2-chloro-3-(pyrrol-1-yl)phenyl]-1,4-dihydro-2,6-dimethyl-pyridine-3,5-dicarboxylate Isopropyl 2-methoxyethyl (−)-4-[2-chloro-3-(pyrrol-1yl)phenyl]-1,4-dihydro-2,6-dimethyl-pyridine-3,5-dicarboxylate Isopropyl 2-methoxyethyl 4-[2-chloro-5-(pyrrol-1-yl)phenyl]-1,4-dihydro-2,6-dimethyl-pyridine-3,5-dicarboxylate Isopropyl 2-methoxyethyl 4-[2-chloro-3-(2,5-dimethyl-pyrrol-1-yl)phenyl]-1,4-dihydro-2,6-dimethyl-pyridine-3,5-dicarboxylate Isopropyl 2-methoxyethyl 4-[2-chloro-5-(2,5-dimethyl-pyrrol-1-yl)phenyl]-1,4-dihydro-2,6-dimethyl-pyridine-3,5-dicarboxylate Isopropyl cyclopentyl 4-[2-chloro-5-(2,5-dimethylpyrrol-1-yl)phenyl]-1,4-dihydro-2,6-dimethyl-pyridine-3,5-dicarboxylate Cyclopentyl-2-methoxyethyl 1,4-dihydro-2,6-dimethyl-4-[3-(pyrrol-1-yl)phenyl]-pyridine-3,5-dicarboxylate.

Processes have furthermore been found for the preparation of the compounds of the general formula (I) according to the invention, characterized in that

[A] aldehydes of the general formula (II)

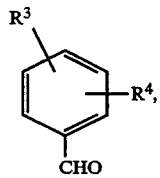

(II)

in which
$R^3$ and $R^4$ have the above-mentioned meaning,
are first reacted with acetoacetic acid esters of the general formula (III)

(III)

in which
$R^2$ has the above-mentioned meaning,
if appropriate with isolation of the benzylidene compound,
and the products are then reacted with 2-aminocrotonic acid esters of the general formula (IV)

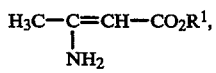

(IV)

in which
$R^1$ has the above-mentioned meaning,
in inert solvents in the presence of a base and if appropriate acids,
or

[B] in the case where the substituent $R^4$ represents a 1,3,4-oxadiazolyl radical,
compounds of the general formula (V)

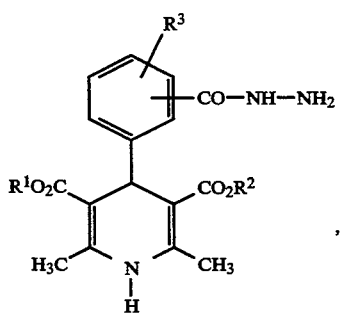

(V)

in which
$R^1$, $R^2$ and $R^3$ have the above-mentioned meaning,
are reacted with 1,1,1-trialkoxyalkanes, and in the case of an amino-substituted oxadiazolyl radical, the products are reacted with cyanogen bromide or cyanogen chloride in the presence of bases,
or

[C] in the case where $R^4$ represents a 1,2,4-oxadiazolyl radical,
compounds of the general formula (VI)

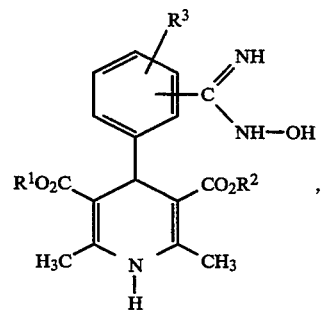

(VI)

in which
$R^1$, $R^2$ and $R^3$ have the above-mentioned meaning, are reacted with 1,1,1-trialkoxyalkanes, carboxylic acid chlorides or carboxylic acid anhydrides in inert solvents, if appropriate in the presence of bases,
or

[D] in the case where $R^4$ represents the tetrazolyl radical,
compounds of the general formula (VII)

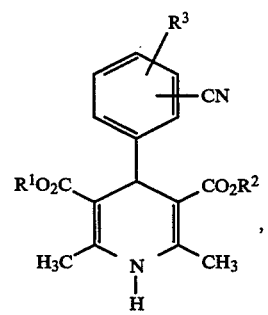

(VII)

in which
$R^1$, $R^2$ and $R^3$ have the above-mentioned meaning,
are reacted with sodium azide in inert solvents in the presence of ammonium chloride,
or

[E] in the case where $R^4$ denotes a pyrrole radical bonded via the nitrogen atom,
compounds of the general formula (VIII)

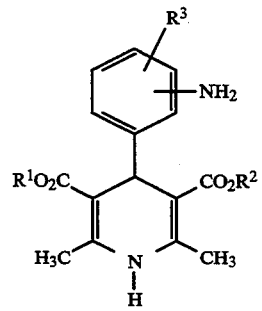

(VIII)

in which
$R^1$, $R^2$ and $R^3$ have the above-mentioned meaning, are reacted with 1,4-dicarbonyl compounds of the general formula (IX) or di (C$_1$-C$_4$)alkoxyfurans of the general formula (X)

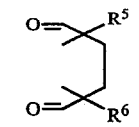
(IX)

or

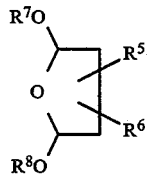
(X)

in which
R$^5$ and R$^6$ have the above-mentioned meaning
and
R$^7$ and R$^8$ are identical or different and denote C$_1$-C$_4$-alkyl,
in inert solvents in the presence of acids, or
[F] compounds of the general formula (XI)

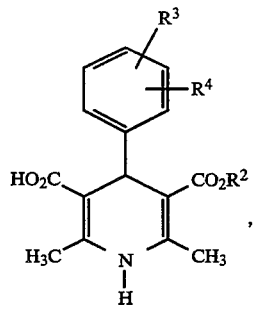
(XI)

in which
R$^2$, R$^3$ and R$^4$ have the above-mentioned meaning,
are reacted with the corresponding alcohols, if appropriate via a reactive acid derivative, in the presence of a base, wherein by using the enantiomerically pure derivatives of the compounds of the general formula (XI), the corresponding enantiomers of the general formula (I) are obtained.

The processes according to the invention can be illustrated by way of example by the following equation:

[A]

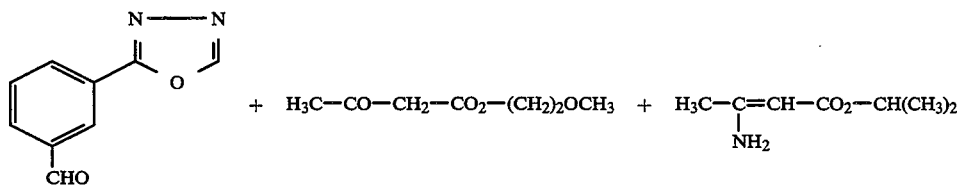

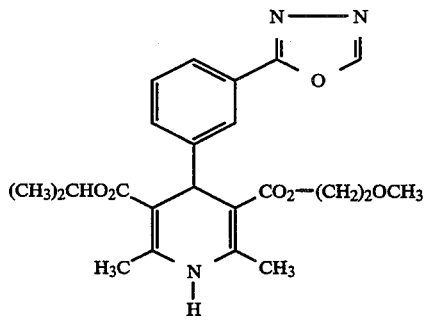

[B]

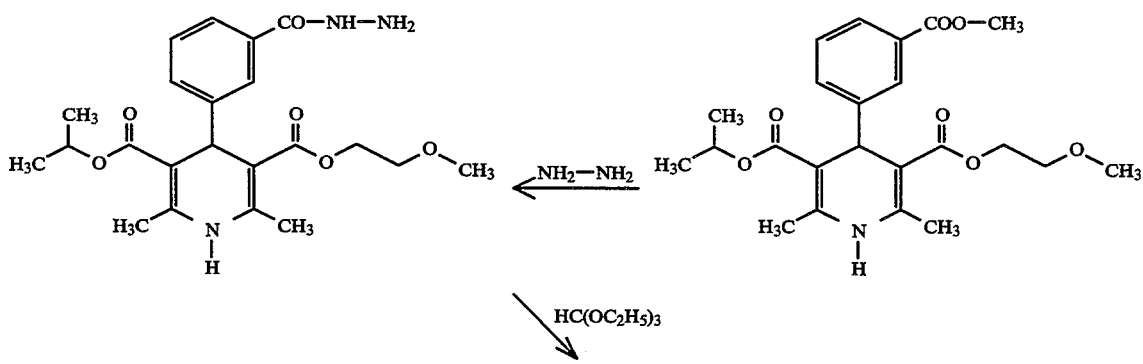

-continued
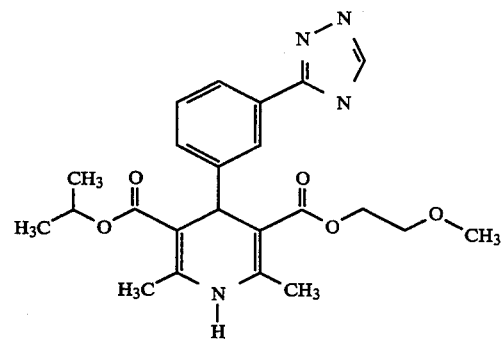
[C]
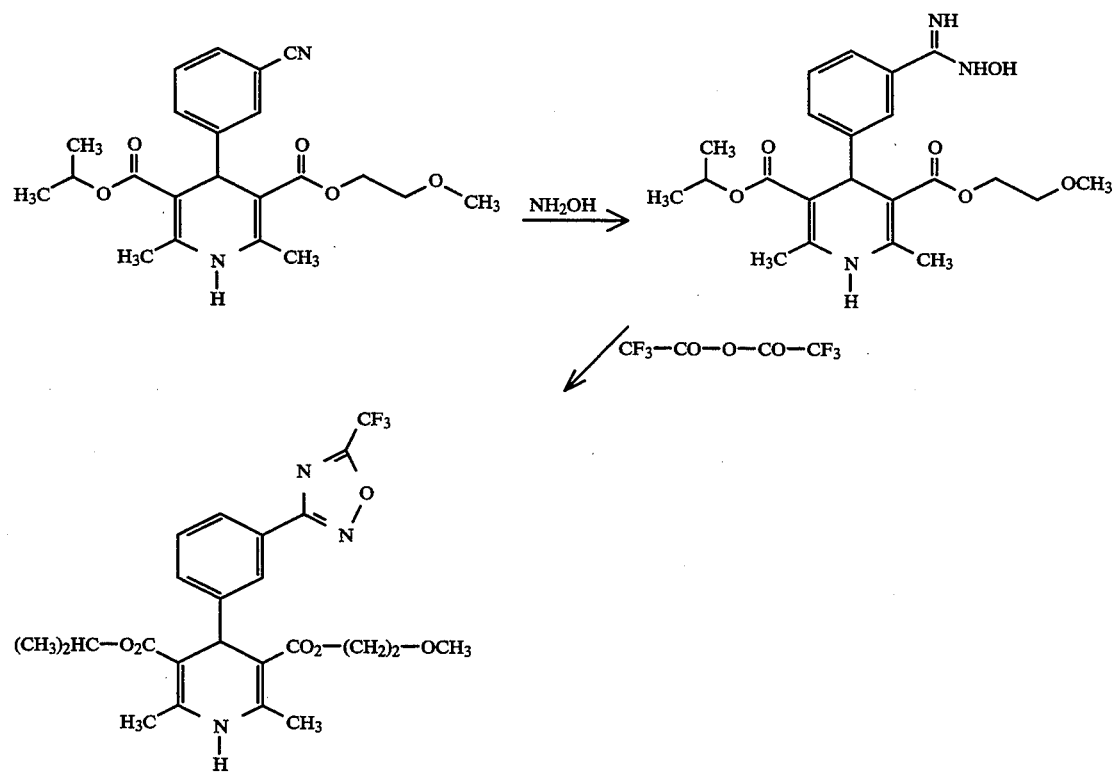
[D]
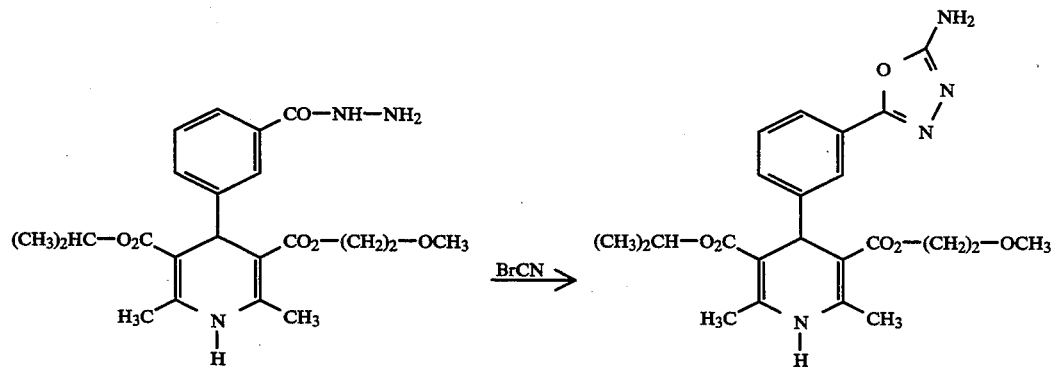

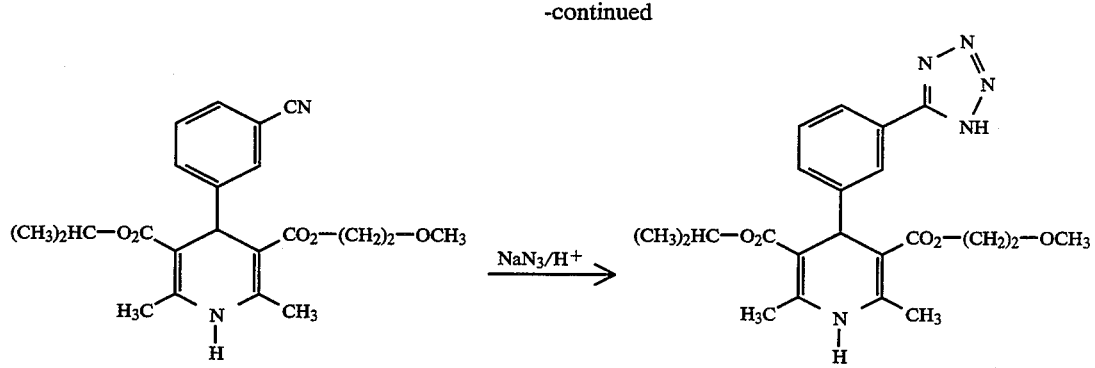

[E]

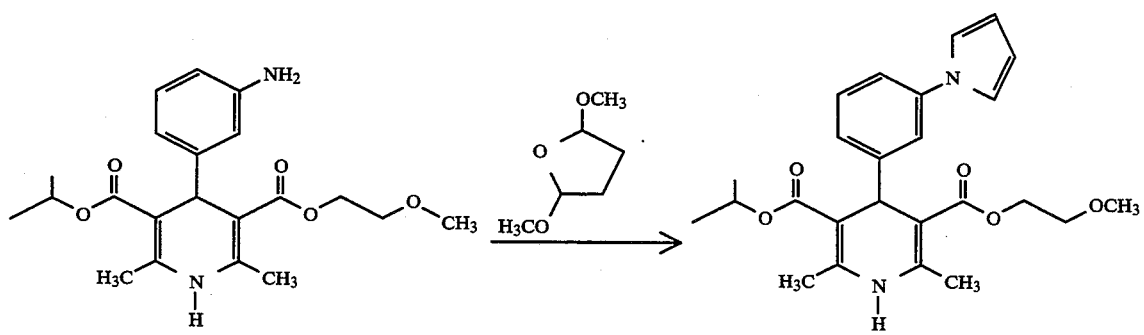

[F]

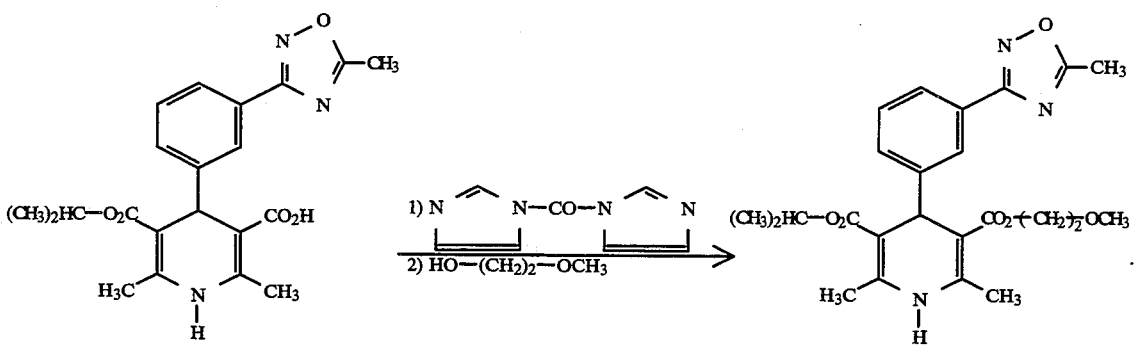

Suitable solvents for processes [A] to [E] here are all the inert organic solvents which do not change under the reaction conditions. These include, preferably, alcohols, such as methanol, ethanol, propanol or isopropanol, or ethers, such as diethyl ether, dioxane, tetrahydrofuran, glycol dimethyl ether or diethylene glycol dimethyl ether, acetonitrile, or amides, such as hexamethylphosphoric acid triamide or dimethylformamide, or acetic acid, or halogenated hydrocarbons, such as methylene chloride or carbon tetrachloride, or hydrocarbons such as benzene or toluene. It is likewise possible to use mixtures of the solvents mentioned. Isopropanol, ethanol, tetrahydrofuran, methanol, dioxane and dimethylformamide are preferred.

Suitable solvents for process [F] are the above-mentioned solvents with the exception of the alcohols.

Suitable bases are in general alkali metal hydrides or alcoholates, such as, for example, sodium hydride or potassium tert-butylate, or cyclic amines, such as, for example, piperidine or dimethylaminopyridine, or $C_1$-$C_4$-alkylamines, such as, for example, triethylamine. Piperidine, dimethylaminopyridine, pyridine, sodiumhydride and potassium tert-butylate are preferred, depending on the particular reaction steps.

Suitable acids in the case of process [A] are organic $C_1$-$C_3$-carboxylic acids, such as, for example, acetic acid or propionic acid. Acetic acid is preferred.

Suitable acids in the case of process [E] are organic $C_1$-$C_3$-carboxylic acids, such as, for example, acetic acid or propionic acid, or organic $C_1$-$C_7$-sulphonic acids, such as benzenesulphonic acid or toluenesulphonic acid. The organic carboxylic acids can be employed in excess as the solvent, and also catalytically, that is to say in amounts of 0.001-1 molar equivalent, based on compound V; organic sulphonic acids are employed in an amount of 0.001 to 1 equivalent. Acetic acid and toluenesulphonic acid are preferred.

The substances participating in the reaction for carrying out the process according to the invention can be in any desired ratio. In general, however, molar amounts of the reactants are used.

The reaction temperatures can be varied within a substantial range. The reaction is in general carried out between +10° C. and +150° C., preferably between +20° C. and +100° C., in particular at the boiling point of the particular solvent.

The reactions can be carried out under normal pressure, but also under increased or reduced pressure (for example 0.5 to 3 bar). They are in general carried out under normal pressure.

Some reaction steps are advantageously reacted under an inert gas atmosphere.

The customary reagents are suitable for activating the carboxylic acid, such as inorganic halides, for example thionyl chloride, phosphorus trichloride or phosphorus pentachloride, or carbonyldiimidazole, carbodiimides, such as cyclohexylcarbodiimide or 1-cyclohexyl-3-[2-(N-methylmorpholino)ethyl]carbodiimide p-toluenesulphonate, or N-hydroxyphthalimide or N-hydroxy-benzotriazole.

Enantiomerically pure forms are obtained, for example, by separating diastereomer mixtures of the compounds of the general formula (I), in which $R^2$ or $R^3$ represents an optically active ester radical, by the customary method, and then either carrying out the transesterification directly or first preparing the optically active carboxylic acids and then preparing the enantiomerically pure dihydropyridines by esterification in accordance with process [E].

Suitable chiral ester radicals are all the esters of enantiomerically pure alcohols, such as, for example, 1-phenylethanol, lactic acid, lactic acid esters, mandelic acid, mandelic acid esters, 2-aminoalcohols, sugar derivatives, hydroxyamino acid derivatives and many other enantiomerically pure alcohols.

The diastereomers are in general separated either by fractional crystallization, by column chromatography or by Craig partition. The optimum process must be decided from case to case, and sometimes it is also advantageous to use combinations of the individual processes. Separation by crystallization or Craig partition or a combination of the two processes is particularly suitable.

The enantiomerically pure compounds are also accessible by chromatography of the racemic esters on chiral phases.

The compounds of the general formula (II) are known per se or can be prepared by known methods.

The acetoacetic acid derivatives of the general formula (III) are known or can be prepared by known methods.

The aminocrotonic acid derivatives of the formula (IV) are known or can be prepared by known methods.

The compounds of the general formula (V) are new as concrete representatives of substances and can be prepared, for example, by a process in which compounds of the general formula (XII)

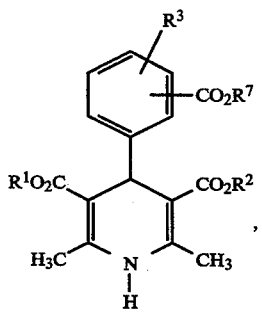
(XII)

in which
$R^1$, $R^2$ and $R^3$ have the above-mentioned meaning and
$R^7$ represents $C_1$–$C_4$-alkyl,
are reacted with hydrazine hydrate in one of the above-mentioned solvents, preferably methanol, and in the presence of KCN in a temperature range from 30° to 100° C., preferably at the reflux temperature and normal pressure.

The compounds of the general formula (VI) are new as concrete representatives of substances and can be prepared, for example, by a process in which compounds of the general formula (VII) are reacted with hydroxylamine or its salts, if appropriate in the presence of bases, such as sodium carbonate, potassium carbonate or triethylamine, in the above-mentioned solvents, preferably in water, alcohols or mixtures thereof, in a temperature range from 30° C. up to the reflux temperature, preferably at the reflux temperature at 100° C. and under normal pressure.

The compounds of the general formula (XII) are new as concrete representatives of substances and can be prepared, for example, first by reaction of the corresponding 3-formylbenzoic acid esters with acetoacetic acid esters in inert solvents, preferably alcohols, in the presence of bases and acids, preferably piperidine and glacial acetic acid, if appropriate with isolation of the ylidene compounds formed, and subsequent reaction with the corresponding 2-aminocrotonic acid esters in a temperature range from +30° C. to +100° C.

The compounds of the general formulae (VII) are likewise known in some cases and can be prepared by customary methods.

The compounds of the general formula (VIII) are new in some cases and can be prepared by a process in which first acetoacetic esters of the general formula (III) and then compounds of the formula (IVa)

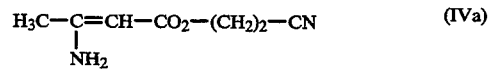

are added to compounds of the general formula (II) as described under process [A], and the dihydropyridinecyanoethyl esters formed are treated with bases, preferably sodium hydroxide or potassium tert-butylate.

The compounds of the general formula (VIII) are new in some cases and can be prepared, for example, by a process in which compounds of the general formula (XIII)

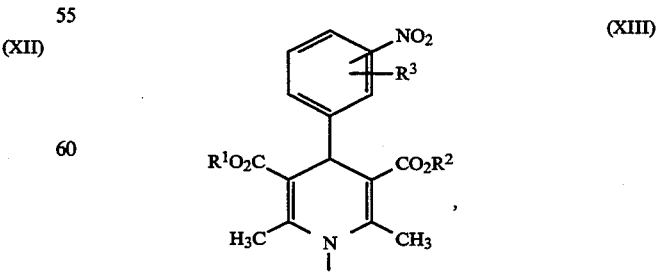
(XIII)

in which
$R^1$, $R^2$ and $R^3$ have the above-mentioned meaning, are hydrogenated in the presence of a catalyst, preferably Raney nickel, in an alcohol, preferably methanol, under normal pressure and at room temperature.

The Compounds of the general formula (XIII) are known in some cases and can then be prepared, for example, first by reaction of the corresponding 3-formylbenzoic acid esters with acetoacetic acid esters in inert solvents, preferably alcohols, in the presence of bases and acids, preferably piperidine and glacial acetic acid, if appropriate with isolation of the ylidene compounds formed, and subsequent reaction with the corresponding 2-aminocrotonic acid esters in a temperature range from $+30°$ C. to $+100°$ C.

The compounds of the general formulae (IX) and (X) are known or can be prepared by customary methods.

The above preparation processes are mentioned merely for illustration. The preparation of the compounds of the general formula (I) is not limited to these processes, but any modification of these processes can be used in the same manner for the preparation of the compounds according to the invention.

The compounds according to the invention exhibit an unforeseeable, valuable pharmacological action spectrum.

The compounds according to the invention are calcium channel ligands having a selectivity for L-type calcium channels of the central nervous system. This selectivity can be demonstrated, for example, by comparison of the binding affinities for DHP binding sites on the rat brain and rat heart.

The compounds have a positive influence on learning and memory performance, as their performance-improving action on rats in typical learning and memory models (for example water labyrinth, Morris labyrinth, passive avoidance, reminiscence tests in automated Skinner boxes) demonstrates. They have an antidepressant potential, as their activity in the Porsolt rat swimming test proves.

Binding assays

The binding affinities for PN 200–110 binding sites in rat brains or rat hearts are determined in accordance with the method of Rampe D. R., Mutledge A., Janis R. A., Triggle D. J.: Can. Journ. Physiol. Pharmacol. 65, (1987) 1452.

Water labyrinth

Old Wistar rats (24 months) are placed at the start position in a plastic tank ($120 \times 50 \times 40$ cm) filled with cold ($14°-15°$) water and subdivided by vertical barriers. To arrive at a ladder which allows the animals to escape from the water, they must swim around these barriers. The time required to discover the way out and the number of errors on the route to the way out are recorded. An error is defined here as swimming into a dead-end or swimming over the boundary line of imaginary squares, into which the tank is subdivided, in the direction away from the way out.

The rats remain in the labyrinth until the exit is discovered, but for not longer than 300 seconds. They are then picked up, dried and warmed under a red lamp. They then return to their home cages. In a typical experiment, two equivalent groups of animals (placebo, test substance in each case $n=15$) are determined by a preliminary test. The animals then undergo 6 test sessions, two per day. The test substances or placebo are administered orally 30 minutes before the experiments. The shortening in the time until the way out is reached, the reduction in the number of errors and the increase in the number of animals which find the way out at all are a measure of the learning- and memory-improving action of the test substances in comparison with placebo.

Porsolt rat swimming test

During a preliminary test, young rats are placed in a glass cylinder (40 cm high, 20 cm diameter) filled to a level of 17 cm with water of 25° C. After 20 minutes in the water, the animals are removed and warmed under a lamp for 30 minutes. In this preliminary test, all the rats attempt to escape from the cylinder, until they freeze in an immobile state after about 15 minutes ("behavioural despair"). The test session starts 24 hours later, the rats being placed in the glass cylinder as on the previous day, but this time for only 5 minutes. The periods of time for which the rats freeze in the immobile state during these 5 minutes are recorded. A rat which performs only minimum propelling movements while upright in the water in order to keep its head above water is regarded as immobile here. The placebo or test substances (0.25, 0.5, 1, 5, 10 mg/kg; $n=6$ per group) are administered orally three times: 23, 5 and 1 hour before the test session (1, 19, 23 hours after the preliminary test). The antidepressant action of the test substances manifests itself in the reduction of the duration of immobility in comparison with the placebo values.

On the basis of their pharmacological properties, the active compounds can be employed for the preparation of medicaments for the treatment of centrally degenerative diseases, such as, for example, occurrences with dementias (multi infarction dementia MID, primary degenerative dementia PDD, presenile and senile Alzheimer's disease, HIV dementia and other forms of dementia), Parkinson's disease or amyotrophic lateral sclerosis.

The active compounds furthermore are suitable for the treatment of disturbances in cerebral performances in old age, organic brain syndrome (OBS) and age-associated memory impairments (AAMI).

They are valuable for the prophylaxis and for combating the consequences of cerebral circulatory disturbances, such as cerebral ischaemias, apoplexies and subarachnoid haemorrhages, and for the treatment of cerebral traumas.

They are suitable for the treatment of depressions and mania. Other fields of use are the treatment of migraine, of neuropathies and of addictions and withdrawal symptoms.

The present invention also includes pharmaceutical formulations which, in addition to inert, non-toxic, pharmaceutically suitable auxiliaries and excipients, comprise one or more compounds of the general formula (I), or which consist of one or more active compounds of the formula (I), and to processes for the preparation of these formulations.

The active compounds of the formula (I) should be present in these formulations in a concentration of 0.1 to 99.5% by weight, preferably 0.5 to 95% by weight of the total mixture.

The pharmaceutical formulations can also comprise other pharmaceutical active compounds in addition to the active compounds of the formula (I).

The above-mentioned pharmaceutical formulations can be prepared in the customary manner by known methods, for example using the auxiliary or excipient substance or substances.

In general, it has proved advantageous to administer the active compound or compounds of the formula (I) in total amounts of about 0.01 to about 100 mg/kg, preferably in total amounts of about 1 mg/kg to 50 mg/kg of body weight every 24 hours, if appropriate in the form of several individual doses, to achieve the desired result.

However, if appropriate, it may be advantageous to deviate from the amounts mentioned, and in particular as a function of the nature and body weight of the subject to be treated, of the behaviour of the individual towards the medicament, of the nature and severity of the disease, of the nature of the formulation and administration, and of the time or interval at which administration takes place.

The particular RF values stated were—unless noted otherwise—determined by thin layer chromatography on silica gel (aluminium foil, silica gel 60 F 254, E. Merck). The substance spots were visualised by viewing under UV light and/or spraying with 1% strength potassium permanganate solution.

The flash chromatography was carried out on silica gel 60, 0.040–0.064 mm, E. Merck. Elution with solvent gradients means: starting with the pure, non-polar solvent mixture component, the polar mobile phase component is admixed to an increasing extent until the desired product is eluted (thin layer chromatography control).

Starting compounds

EXAMPLE I

Isopropyl 2-methoxyethyl 1,4-dihydro-2,6-dimethyl-4-(3-methoxycarbonyl-phenyl)-pyridine-3,5-dicarboxylate

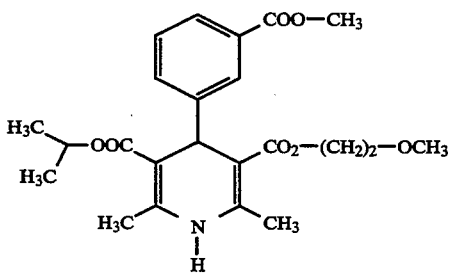

10.0 g (61 mmol) of methyl 3-formylbenzoate, 10.0 g (60 mmol) of 2-methoxyethylacetoacetate, 0.2 ml of glacial acetic acid and 0.4 ml of piperidine are heated at 40° C. in 100 ml of 2-propanol for 2.5 hours. After cooling, the mixture is concentrated and the crude product is purified by flash chromatography (silica gel, toluene/ethyl acetate 20:1 to 1:1). 17.6 g (94 %) of the benzylidene compound are obtained as a yellow oil. 17.6 g (57.5 mmol) of this intermediate product and 8.2 g (75.5 mmol) of isopropyl 3-aminocrotonate in 150 ml of 2-propanol are heated under reflux for 1 hour. The crude product obtained after concentration is purified by chromatography (silica gel, toluene/ethyl acetate 1:0 to 1:1). 19.8 g (80 %) of product of adequate purity for further reaction are thus obtained. The product can be obtained in the form of colourless crystals, melting point 86°–88° C., by triturating with diethyl ether.

The compounds listed in Table I are obtained analogously to the instructions of Example I:

TABLE I

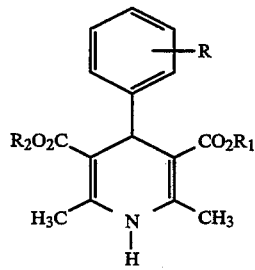

| Ex. No. | R | $R^2$ | $R^1$ | Melting Point °C. | Yield (% of theory) |
|---|---|---|---|---|---|
| II | 3-$CO_2CH_3$ | —$CH(CH_3)_2$ | —$(CH_2)_2$—CN | 119 | 52 |
| III | 3-$CO_2CH_3$ | —$(CH_2)_2OCH_3$ | —$(CH_2)_2$—CN |  | 70 |
| IV | 3-CN | —$CH(CH_3)_2$ | —$(CH_2)_2$—$OCH_3$ | 123–125 | 36 |
| V | 3-$CO_2CH_3$ | —$CH(CH_3)_2$ | —$(CH_2)_2$—$OC_3H_7$ |  | 89 |

EXAMPLE VI

Isopropyl 2-methoxy-ethyl 1,4-dihydro-2,6-dimethyl-4-(3-hydrazinocarbonyl-phenyl)-pyridine-3,5-dicarboxylate

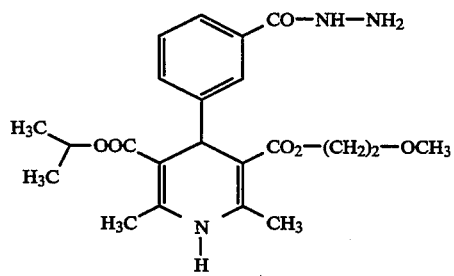

3.0 g (7.0 mmol) of the compound from Example I and 3.0 ml of aqueous hydrazine hydrate solution (64% strength) are dissolved in 30 ml of methanol, and a spatula-tip of potassium cyanide is added. After the mixture has been heated under reflux for 2 hours, a further 3.0 ml of hydrazine hydrate solution are added and the mixture is heated under reflux for a further 60 minutes. The reaction mixture is freed from the solvent in vacuo. Digestion of the residue with ethyl acetate gives 2.3 g (77 %) of colourless crystals. Melting point: 187°–189° C. The substance is stored at +4° C.

EXAMPLE VII

The 2-methoxy-ethyl ester of 1,4-dihydro-2,6-dimethyl-4-(3-methoxycarbonyl-phenyl)-pyridine-3,5-dicarboxylic acid

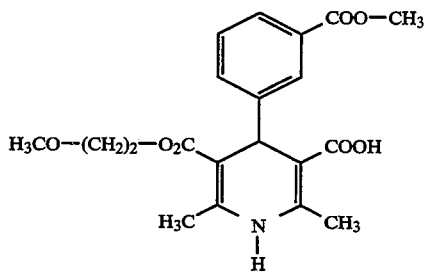

30.4 g (0.27 mol) of potassium tert-butylate are added in portions to 100 g (0.23 mol) of the compound from Example III in 1 l of tetrahydrofuran at room temperature under argon. After 2 hours at room temperature, the mixture is heated to 50° C. and the solution is concentrated to about ⅔ under a gentle vacuum. After dilution with 2 l of ethyl acetate, the mixture is poured onto a mixture of 2 l of water and 30 ml of concentrated hydrochloric acid. After filtration over kieselguhr, the aqueous phase is removed and the organic phase is washed and dried. Stirring the organic phase with Tonsil and concentration gives an oil which solidifies and which is converted into colourless crystals, melting point 152° C. (with evolution of gas) by trituration with diethyl ether.

Yield: 77.4 g (88 %)

The compounds listed in Table II are prepared analogously to the instructions of Example VII:

TABLE II

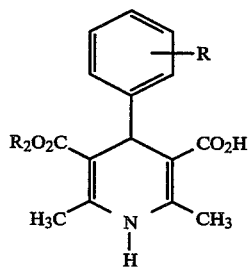

| Ex. No. | R | R² | Starting material | Melting Point °C. | Enantiomer |
|---|---|---|---|---|---|
| VIII | —CO₂CH₃ | —CH(CH₃)₂ | II | about 180 (decomposition) | racemic |
| IX | —CO₂CH₃ | —(CH₂)₂OCH₃ | VII[a)] | oil | (+); |
| X | —CO₂CH₃ | —(CH₂)₂OCH₃ | VII[a)] | oil | (−); $\alpha^{20}_D = -21{,}2$ (c = 1, CH₃OH) |
| XI | —CN | —CH(CH₃)₂ | b) | 132–136 | (−); $\alpha^{20}_D = -22{,}2$ (c = 1, CH₃OH) |
| XII | —CN | —CH(CH₃)₂ | b) | 139–140 | (+); $\alpha^{20}_D = +22{,}1$ (c = 1, CH₃OH) |

[a)] separation by chromatography on chiral phases
[b)] from the racemate by chromatographic separation on chiral phases

EXAMPLE XIII di-(2-Methoxyethyl) 1,4-dihydro-2,6-dimethyl-4-(3-methoxycarbonyl-phenyl)-pyridine-3,5-dicarboxylate

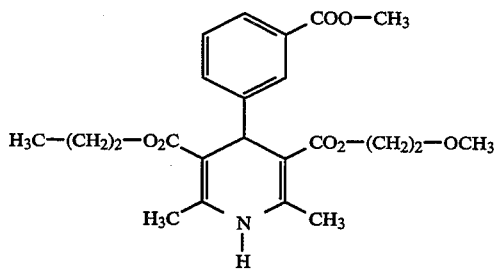

0.16 g (1.0 mmol) of carbonyldiimidazole is added to 0.40 g (1.0 mmol) of the compound from Example VII in 4 ml of absolute tetrahydrofuran, and the mixture is stirred at room temperature overnight. The solvent is stripped off on a rotary evaporator and the residue is taken up in 4 ml of 2-methoxyethanol. A spatula-tip of 4-dimethylaminopyridine is added and the mixture is heated at 80° C. for 24 hours. The crude product which remains after concentration is purified by chromatography (silica gel, toluene/ethyl acetate 10:1 to 3:1). 0.35 g (78%) of the title compound are obtained as an oil.

The compounds listed in Table III are prepared analogously to the instructions of Example XIII:

TABLE III

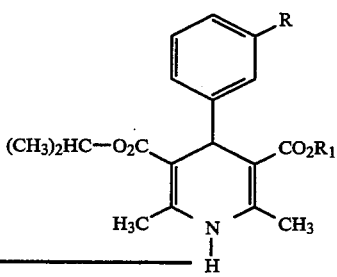

| Ex. No. | R | R¹ | Starting material | Melting Point °c/R$_f$* |
|---|---|---|---|---|
| XIV | —CH(CH₃)₂ | —CH(CH₃)₂ | VIII | oil[a)] |
| XV | —CO₂CH₃[b)] | —(CH₂)₂OCH₃ | IX | 71–72 |
| XVI | —CO₂CH₃[c)] | —(CH₂)₂OCH₃ | X | 71–72 |
| XVII | —CN[d)] | —(CH₂)₂OCH₃ | XI | 127–128 |

TABLE III-continued

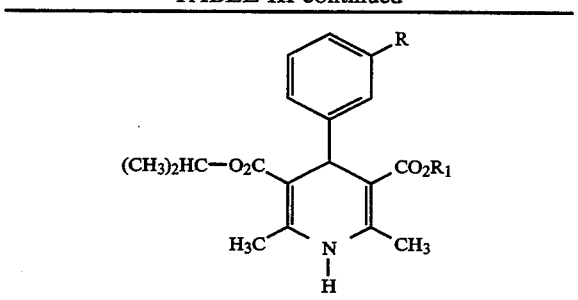

| Ex. No. | R | R$^1$ | Starting material | Melting Point °c/R$_f$* |
|---|---|---|---|---|
| XVIII | —CN[e] | —(CH$_2$)$_2$OCH$_3$ | XII | 127–128 |

[a] R$_f$ (toluene/ethyl acetate 1:1) = 0.54
[b] $\alpha_D^{20}$ = +33.7 (c = 1, methanol)
[c] $\alpha_D^{20}$ = −33.1 (c = 1, methanol)
[d] $\alpha_D^{20}$ = +14.4 (c = 1, chloroform)
[e] $\alpha_D^{20}$ = −13.3 (c = 1, chloroform)

The compounds listed in Table IV are prepared analogously to the instructions of Example VI:

TABLE IV

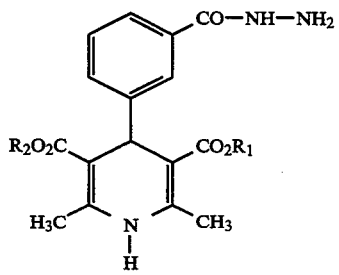

| Ex. No. | R$^2$ | R$^1$ | Melting Point °C. | Enantiomer | Starting material |
|---|---|---|---|---|---|
| XIX | —(CH$_2$)$_2$OCH$_3$ | —(CH$_2$)$_2$OCH$_3$ | 124–125 | | XIII |
| XX | —CH(CH$_3$)$_2$ | —CH(CH$_3$)$_2$ | 110 (decomposition) | | XIV |
| XXI | —(CH$_2$)$_2$OCH$_3$ | —CH(CH$_3$)$_2$ | 155–157 | pure | XV |
| XXII | —(CH$_2$)$_2$OCH$_3$ | —CH(CH$_3$)$_2$ | 154–156 | pure | XVI |
| XXIII | —(CH$_2$)$_2$OC$_3$H$_7$ | —CH(CH$_3$)$_2$ | Öl | | V |

EXAMPLE XXIV

Isopropyl 2-methoxyethyl 1,4-dihydro-2,6-dimethyl-4-(3-N-hydroxycarbonimidamido-phenyl)-pyridine-3,5-dicarboxylate 3.98 g (10 mmol) of the compound from Example IV, 1.40 g (20 mmol) of hydroxylamine hydrochloride and 1.40 g (10 mmol) of potassium carbonate are suspended in 40 ml of a 4:1 ethanol/water mixture and the suspension is heated under reflux overnight. The reaction mixture is concentrated and the residue is leached out with ethyl acetate. After concentration, 4.2 g of title compound (97%) are obtained from the extracts as an amorphous solid, which is further reacted in the crude form.

The compounds listed in Table V are obtained analogously to Example XXIV:

TABLE V

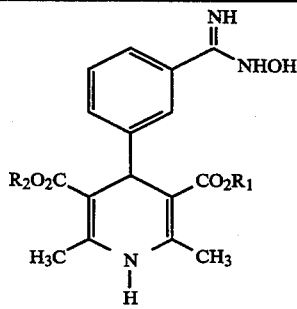

| Ex. No. | R$^2$ | R$^1$ | Melting Point °C. | Enantiomer | Starting material |
|---|---|---|---|---|---|
| XXV | —(CH$_2$)$_2$OCH$_3$ | —CH(CH$_3$)$_2$ | amorphous | pure | XVII |
| XXVI | —(CH$_2$)$_2$OCH$_3$ | —CH(CH$_3$)$_2$ | amorphous | pure | XVIII |

EXAMPLE XXVII

Isopropyl 2-methoxyethyl 4-(3-amino-2-chlorophenyl)-1,4-dihydro-2,6-dimethyl-pyridine-3,5-dicarboxylate

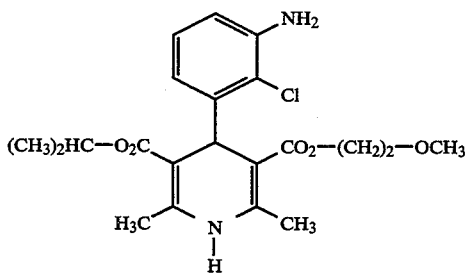

27.5 g (61 mmol, purity 96.5%) of isopropyl 2-methoxyethyl 4-(2-chloro-3-nitrophenyl)-1,4-dihydro-2,6-dimethyl-pyridine-3,5-dicarboxylate, obtained by reaction of equimolar amounts of 2-chloro-3-nitrobenzaldehyde, isopropyl β-aminocrotonate and methoxyethyl acetoacetate in 2-propanol at the reflux temperature, are suspended in 500 ml of methanol and hydrogenated in the presence of Raney nickel (about 1.5 g, water-moist) under normal pressure and temperature until the end of the uptake of hydrogen (1 hour). The catalyst is filtered off and the residue obtained after concentration is purified by flash chromatography (toluene/ethyl acetate 1:0→5:1). Crystallization from toluene gives 24.0 g (93% of theory) of the title compound of melting point 118°–122° C.

EXAMPLE XXVIII

Isopropyl 2-methoxyethyl 4-(5-amino-2-chlorophenyl)-1,4-dihydro-2,6-dimethyl-pyridine-3,5-dicarboxlate

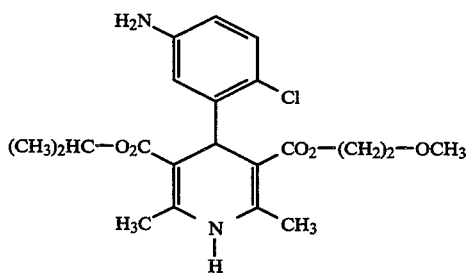

The title compound is obtained from 22.8 g (50 mol) of isopropyl 2-methoxyethyl 4-(2-chloro-5-nitrophenyl)-1,4-dihydro-2,6-dimethyl-pyridine-3,5-dicarboxylate analogously to the instructions of Example XXVII. $R_f=0.23$ (toluene/ethyl acetate 1:1)

EXAMPLE XXIX

2-Cyanoethyl 2-methoxyethyl 4-(3-aminophenyl)-1,4-dihydro-2,6-dimethyl-pyridine-3,5-dicarboxylate

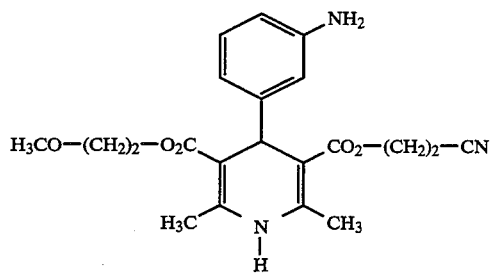

The title compound is obtained analogously to Example XXVII from 49.0 g (114 mmol) of 2-cyanoethyl 2-methoxyethyl 1,4-dihydro-2,6-dimethyl-4-(3-nitrophenyl)-pyridine-3,5-dicarboxylate and is further reacted directly as the crude product.

EXAMPLE XXX

Isopropyl 2-methoxyethyl 4-(3-aminophenyl)-1,4-dihydro-2,6-dimethyl-pyridine-3,5-dicarboxylate

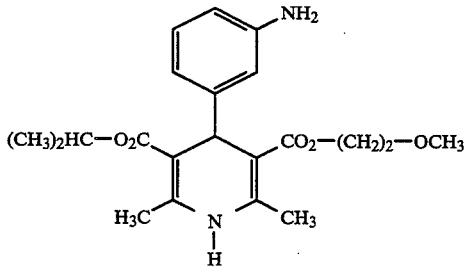

The title compound is obtained analogously to Example XXVII by reaction of 12.6 g (30.1 mmol) of isopropyl 2-methoxyethyl 1,4-dihydro-2,6-dimethyl-4-(3-nitrophenyl)-pyridine-3,5-dicarboxylate. Melting point ° C: 138°–140° C.

EXAMPLE XXXI

The isopropyl monoester of 4-(2-chloro-3-nitrophenyl)-1,4-dihydro-2,6-dimethyl-pyridine-3,5-dicarboxylic acid

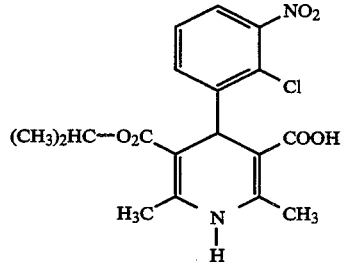

45.6 g (34%) of 2-cyanoethyl isopropyl 4-2-chloro-3-nitrophenyl)-1,4-dihydro-2,6-dimethyl-pyridine-3,5-dicarboxylate are obtained from 55.7 g (300 mmol) of 2-chloro-3-nitrobenzaldehyde, 43.2 g (300 mmol) of isopropyl acetoacetate and 46.2 g (300 mmol) of 2-cyanoethyl 3-aminocrotonate in the customary manner, and are dissolved in 500 ml of dimethoxyethane, and 5.3 g of sodium hydroxide in 100 ml of water are added. After 2 hours at room temperature, the mixture is poured onto 6 l of ice-water, to which 20 ml of concentrated hydrochloric acid are added. The precipitate which separates out is filtered off with suction after 30 minutes, washed and dried. 39.2 g of almost colourless crystals are thus obtained.
Melting point: 159° C.

EXAMPLE XXXII

Isopropyl 2-methoxyethyl 4-(3-amino-2-chlorophenyl)-1,4-dihydro-2,6-dimethyl-pyridine-3,5-dicarboxylate (isomer A)

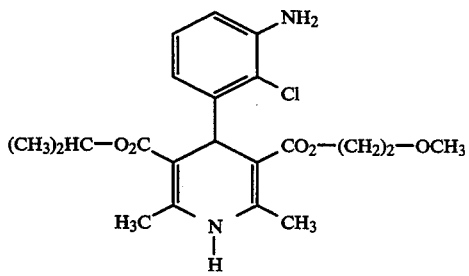

The pure (+)-enantiomer ($\alpha_d^{20}$=+21.0; c=1, tetrahydrofuran) can be obtained from Example XXXI by chromatography on a chiral support material; 2.4 g (15 mmol) of carbonyldiimidazolide are added to 5.9 g (15 mmol) of this compound in 60 ml of tetrahydrofuran and the mixture is stirred at 60° C. for 1 hour. After concentration, 40 ml of 2-methoxyethanol are added and the mixture is stirred at 80° C. for 18 hours. The solvent is removed and the residue is purified by flash chromatography (toluene/ethyl acetate 1:0 to 3:1). Crystallization from toluene/cyclohexane gives 4.3 g (63% of theory) of isopropyl 3-methoxyethyl 4-(2-chloro-3-nitrophenyl-1,4-dihydro-2,6-dimethyl-pyridine-3,5-dicarboxylate ($\alpha_D^{20}$=−10.1; c=0.9, CHCl$_3$).

4.0 g (quantitative) of the title compound are obtained therefrom as a crude product, analogously to Example I, which is further reacted directly.

Preparation Examples

EXAMPLE I

Isopropyl 2-methoxyethyl 1,4-dihydro-2,6-dimethyl-4-[3-(1,3,4-oxadiazol-2-yl)-phenyl]-pyridine-3,5-dicarboxylate

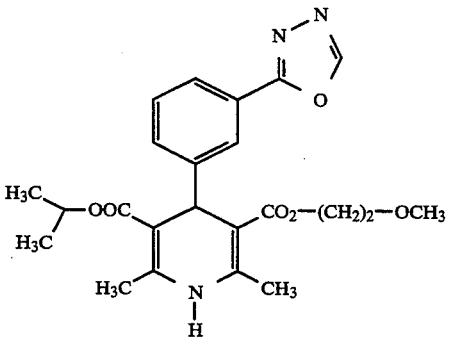

20 ml of triethoxymethane are added to 4.4 g (10 mmol) of the compound from Example VI and the mixture is heated under reflux for 30 minutes, the ethanol formed being distilled off continuously. After concentration, the crude product is isolated by chromatography (silica gel, toluene/ethyl acetate 1:0 to 1:1). Trituration with diethyl ether gives crystals of melting point 134°-136° C., which are recrystallized from toluene. This gives 2.0 g (44%) of the title compound in the form of colourless crystals.
Melting point: 138°-140° C.

The compounds listed in Tables 1 and 2 are prepared analogously to the instructions of Example 1:

TABLE 1

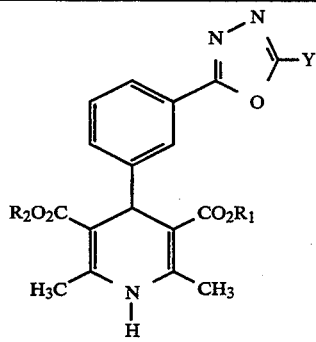

| Ex. No. | Y | R$^2$ | R$^1$ | Melting Point °C. | Starting material |
|---|---|---|---|---|---|
| 2 | —NH$_2$[a] | —CH(CH$_3$)$_2$ | —(CH$_2$)$_2$OCH$_3$ | 202-205 | VI |
| 3 | H | —(CH$_2$)$_2$OCH$_3$ | —(CH$_2$)$_2$OCH$_3$ | 201-202 | XIX |
| 4 | —CH$_3$[b] | —(CH$_2$)$_2$OCH$_3$ | —CH(CH$_3$)$_2$ | 136-138 | VI |
| 5 | H | —CH(CH$_3$)$_2$ | —CH(CH$_3$)$_2$ | 132-133 | XX |
| 6 | H[c] | —CH(CH$_3$)$_2$ | —(CH$_2$)$_2$OCH$_3$ | 154-155 | XXI |
| 7 | —CH$_3$[b,d] | —CH(CH$_3$)$_2$ | —(CH$_2$)$_2$OCH$_3$ | 132-133 | XXI |
| 8 | H[e] | —CH(CH$_3$)$_2$ | —(CH$_2$)$_2$OCH$_3$ | 154-155 | XXII |
| 9 | —CH$_3$[b,f] | —CH(CH$_3$)$_2$ | —(CH$_2$)$_2$OCH$_3$ | 132-133 | XII |
| 10 | H | —CH(CH$_3$)$_2$ | —(CH$_2$)$_2$OC$_3$H$_7$ | 142-143 | XXIII |

[a] reaction with 1 equivalent of cyanogen bromide in methanol; 1 hour, room temperature
[b] reaction with 1,1,1-triethoxyethane; 6 hours, 120°
[c] $\alpha_D^{20}$ = +27.8 (c = 1, methanol)
[d] $\alpha_D^{20}$ = +30.2 (c = 1, methanol)
[e] $\alpha_D^{20}$ = −28.5 (c = 1, methanol)
[f] $\alpha_D^{20}$ = −30.6 (c = 1, methanol)

TABLE 2

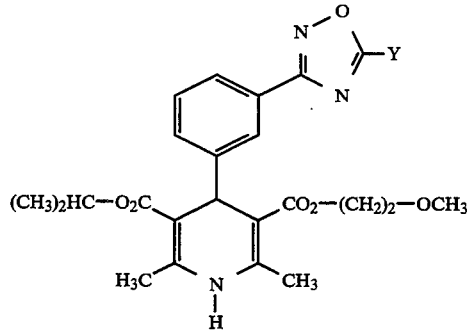

| Ex. No. | Y | Melting Point °C. | Starting material |
|---|---|---|---|
| 11 | H | 120–122 | XXIV |
| 12 | —CH₃ [b] | 114–115 | XXIV |
| 13 | —CO₂C₂H₅ [g] | 152–153 | XXIV |
| 14 | —CO₂C₂H₅ [g,h] | 150–151 | XXV |
| 15 | —CO₂C₂H₅ [g,i] | 150–151 | XXVI |
| 16 | —CF₃ [j] | 91–93 | XXIV |

[b] reaction with 1,1,1-triethoxyethane; 6 hours, 120°

[g] reaction with oxalic acid ethyl ester chloride and pyridine in the presence of molecular sieve 4A in methylene chloride; overnight, room temperature

[h] $a_D^{20}$ = +28.4 (c = 1, chloroform)

[i] $a_D^{20}$ = −27.6 (c = 1, chloroform)

[j] reaction with 1 equivalent of trifluoroacetic anhydride and 1 equivalent of pyridine in the presence of molecular sieve 4A in methylene chloride overnight at room temperature. The substance is sensitive to light.

EXAMPLE 17

Isopropyl 2-methoxyethyl 1,4-dihydro-2,6-dimethyl-4-(3-tetrazol-5-yl-phenyl)-pyridine-3,5-dicarboxylate

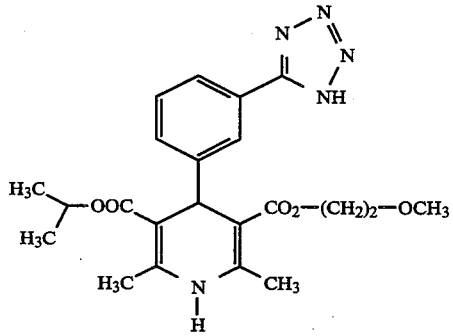

0.71 g (11 mmol) of sodium azide and 0.59 g (11 mmol) of ammonium chloride are added to 3.98 g (10 mmol) of the compound from Example IV in 40 ml of dry dimethylformamide After 16 hours at 100° C. the cooled mixture is poured onto 120 ml of water. The solution is brought to pH 1 with concentrated hydrochloric acid and extracted several times with ethyl acetate. Drying and concentration of the organic phase gives the crude product, which is purified by two chromatography operations (silica gel, methylene chloride/2-propanol 1:0 to 1:1 and toluene/ethyl acetate 1:0 to 0:1). Trituration of the evaporated eluates gives 1.80 g. (41%) of colourless crystals, melting point >129° C. (with evolution of gas).

EXAMPLE 18

Isopropyl 2-methoxyethyl 1,4-dihydro-2,6-dimethyl-4-[(3-pyrrol-1-yl)phenyl]-3,5-dicarboxylate

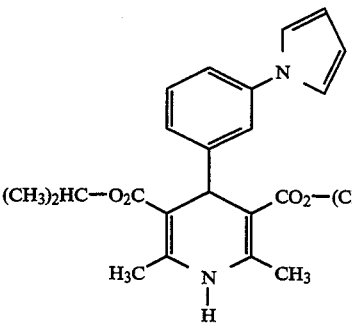

3.2 g (8.2 mmol) of the compound from Example XXX are dissolved in 11 ml of glacial acetic acid under argon, and 1.1 g (8.2 mmol) of 2,5-dimethoxytetrahydrofuran are added. The mixture is heated first at 40° C. for 30 minutes and then at 60° C. for 30 minutes. 100 ml of chloroform and the same amount of 2,5-dimethoxytetrahydrofuran again are added. The azeotrope of methanol/chloroform is distilled off; a further 8.2 mmol of 2,5-dimethoxytetrahydrofuran are added to the reaction mixture, which has been concentrated to 50 ml. After 2 hours under reflux, the mixture is concentrated and the residue is taken up in 4 ml of glacial acetic acid. After addition of 1.1 g (8.2 mmol) of 2,5-dimethoxytetrahydrofuran, the mixture is heated at 90° C. for 30 minutes. After cooling, it is diluted with 100 ml of ethyl acetate and poured onto saturated sodium bicarbonate solution. After drying and concentration, the organic phase gives 6.0 g of an oil, which is purified by flash chromatography (toluene/ethyl acetate 3:1). 1.9 g of oil are obtained, which is converted into 1.1 g of colourless crystals (30% of theory) of melting point 117°–119° C. by trituration with diisopropyl ether.

The compounds listed in Table 3 are obtained in the same manner:

TABLE 3

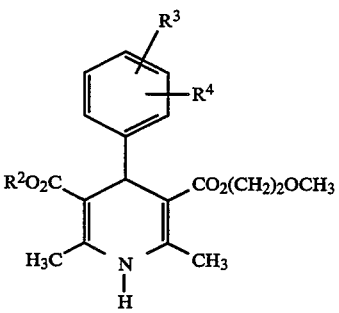

| Ex. No. | R⁴ | R³ | R² | Melting Point °C. |
|---|---|---|---|---|
| 19 [a] | 3-N (pyrrol) | | 2-Cl | —CH(CH₃)₂ | 127 |
| 20 [b] | 5-N (pyrrol) | | 2-Cl | —CH(CH₃)₂ | 144–145 |

TABLE 3-continued

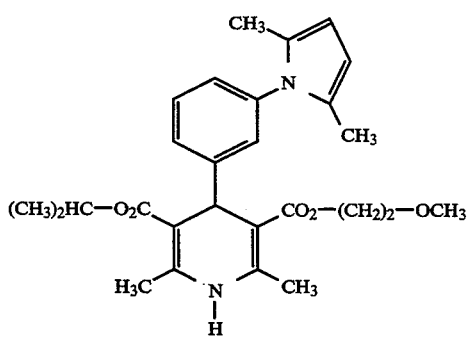

| Ex. No. | R⁴ | R³ | R² | Melting Point °C. |
|---|---|---|---|---|
| 21[c) | 3-N-pyrrolyl | H | —CH₂CH₂CN | oil |
| 22[d) | 3-N-pyrrolyl | 2-Cl | —CH(CH₃)₂ | 105 |
| 23[e) | 3-N-pyrrolyl | 2-Cl | —CH(CH₃)₂ | 105 |

[a)] starting material: Example XXVII
[b)] starting material: Example XXVIII
[c)] starting material: Example XXIX
[d)] $\alpha_D^{20} = -23.7$ (c = 1, CH₃OH); from Example XXXII
[e)] $\alpha_D^{20} = +26.1$ (c = 1, CH₃OH); from Example XXXIII

EXAMPLE 24

Isopropyl 2-methoxyethyl 1,4-dihydro-2,6-dimethyl-4-[3-(2,5-dimethyl-pyrrol-1-yl)phenyl]-pyridine-3,5dicarboxylate

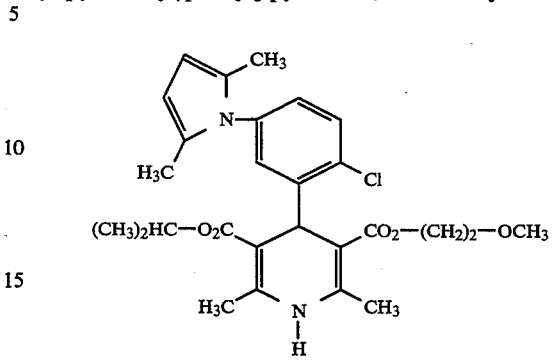

A spatula-tip of p-toluenesulphonic acid and 1.4 g (12 mmol) of 2,5-hexanedione are added to 3.9 g (10 mmol) of the compound from Example XXX in 40 ml of toluene. After 30 minutes at 120° C., the mixture is filtered over a little silica gel and the filtrate is concentrated. The crude product is purified by flash chromatography (toluene/ethyl acetate 2:1). The resulting oil (2.3 g) is triturated with diethyl ether in the cold. After addition of cyclohexane, the crystals which separate out are separated off.
Yield: 0.52 g (11% of theory)
Melting point 106°–107° C.

EXAMPLE 25

Isopropyl 2-methoxyethyl 4-[2-chloro-5-(2,5-dimethyl-pyrrol-1-yl)phenyl]-pyridine-3,5-dicarboxylate

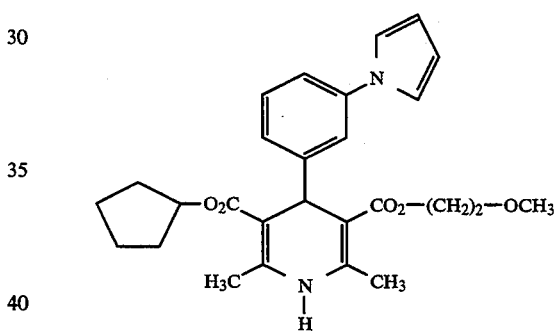

The title compound is prepared analogously to Example 24 from 3.6 g (8.6 mmol) of the compound from EXAMPLE XXVIII.
Melting point ° C.: 147°–149° C.

EXAMPLE 26

Cyclopentyl 2-methoxyethyl 1,4-dihydro-2,6-dimethyl-4-[(3-pyrrol-1-yl)phenyl]pyridine-3,5-dicarboxylate 70 ml of 1M sodium hydroxide solution are added to 15.5 g (34.5 mmol) of the compound from Example 21 in 150 ml of dimethoxyethane and the mixture is stirred at 50° C. for 45 minutes. The batch, which has been cooled to room temperature, is extracted several times with diethyl ether. The aqueous phase is carefully acidified with concentrated hydrochloric acid. The crude product which has precipitated is dried over phosphorus pentoxide in vacuo. Recrystallization from 2-propanol and working up of the mother liquors twice gives 7.1 g (54% of theory) of the 2-methoxyethyl monoester of 1,4-dihydro-2,6-dimethyl-4-[(3-pyrrol-1-yl)phenyl]-pyridine-3,5-dicarboxylate acid, which are further reacted as the crude product.

1.1 g (6.8 mmol) of carbonyldiimidazole are added to 3.0 g (7.6 mmol) of this crude product in 30 ml of tetrahydrofuran and the mixture is stirred at 80° C. for 45 minutes. After the solvent has been removed in vacuo, the residue is taken up in 10 ml of cyclopentanol, and a spatula-tip of 4-dimethylaminopyridine is added. The mixture is stirred at 100° C. for 2 hours. Chromatography over silica gel using cyclohexane/ethyl acetate 3:1 and subsequent stirring of the crude product gives, after working up of the mother liquors, 0.73 g (23% of theory) of colourless crystals. Melting point: 124° C.

We claim:

1. A 4-Heterocyclophenyl-substituted dihydropyridine of the formula-(I)

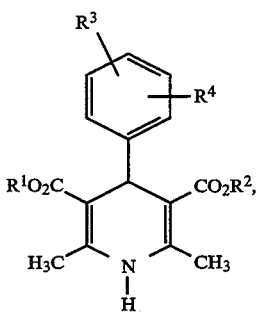

in which $R^1$ and $R^2$ are identical or different and represent cycloalkyl having 3 to 8 carbon atoms, or represent straight-chain or branched alkyl having up to 8 carbon atoms, which is optionally substituted by straight-chain or branched alkoxy having up to 6 carbon atoms, cyano, cycloalkyl having 3 to 8 carbon atoms or aryloxy having 6 to 10 carbon atoms, which can in turn be mono-, di- or trisubstituted by identical or different substituents from the group consisting of halogen, cyano and straight-chain or branched alkyl and alkoxy having up to 6 carbon atoms, $R^3$ represents hydrogen, halogen, trifluoromethyl or cyano, and $R^4$ represents a 1,2,4-oxadiazolyl or 1,3,4-oxadiazolyl radical; which is bonded via a ring carbon atom and is optionally substituted by hydroxyl, straight-chain or branched alkyl or alkoxycarbonyl having in each case up to 6 carbon atoms, trifluoromethyl, halogen, carboxyl or a group of the formula $-NR^5R^6$, wherein $R^5$ and $R^6$ are identical or different and denote hydrogen or straight-chain or branched alkyl or alkoxycarbonyl having in each case up to 4 carbon atoms, 2. A 4-Heterocyclophenyl-substituted dihydropyridine according to claim 1, wherein $R^1$ and $R^2$ are identical or different and represent cyclopropyl, cyclopentyl, cyclohexyl or cycloheptyl, or represent straight-chain or branched alkyl having up to 6 carbon atoms, which is optionally substituted by straight-chain or branched alkoxy having up to 4 carbon atoms, cyano, cyclopropyl, cyclopentyl, cyclohexyl, cycloheptyl or phenoxy, which can in turn be mono-, di- or trisubstituted by identical or different substituents from the group consisting of fluorine, cyano and straight-chain or branched alkyl and alkoxy having in each case up to 4 carbon atoms, $R^3$ represents hydrogen, fluorine, chlorine, bromine, trifluoromethyl or cyano, and $R^4$ represents a 1,2,4-oxadiazolyl or 1,3,4-oxadiazolyl radical which is bonded via a ring carbon atom and is optionally substituted by hydroxyl, straight-chain or branched alkyl or alkoxycarbonyl having in each case up to 4 carbon atoms, trifluoromethyl, fluorine, chlorine or a group of the formula $-NR^5R^6$, wherein $R^5$ and $R^6$ are identical or different and denote hydrogen or straight-chain or branched alkyl or alkoxycarbonyl having in each case up to 3 carbon atoms, or a salt thereof.

3. A 4-Heterocyclophenyl-substituted dihydropyridine according to claim 1, wherein $R^1$ and $R^2$ are identical or different and represent cyclopentyl, cyclohexyl or cycloheptyl, or represent straight-chain or branched alkyl having up to 4 carbon atoms, which is optionally substituted by methoxy, propoxy, cyclopentyl, cyclohexyl or cycloheptyl, $R^3$ represents hydrogen, chlorine, trifluoromethyl or cyano, and $R^4$ represents a 1,2,4-oxadiazolyl or 1,3,4-oxadiazolyl radical which is bonded via a ring carbon atom and is optionally substituted by straight-chain or branched alkyl or alkoxycarbonyl having in each case up to 3 carbon atoms, trifluoromethyl, fluorine, chlorine or amino, or a salt thereof.

4. A 1,2,4- and 1,3,4-oxadiazolyl-phenyl-substituted dihydropyridine selected from the group consisting of:

Isopropyl 2-methoxyethyl 1,4-dihydro-2,6-dimethyl-4-[3-(1,2,4-oxadiazol-3-yl)phenyl]-pyridine-3,5-dicarboxylate Isopropyl 2-methoxyethyl 4-[3-(5-ethoxycarbonyl-1,2,4-oxadiazol-3-yl)-phenyl]-1,4-dihydro-2,6-dimethyl-pyridine-3,5-dicarboxylate Isopropyl 2-methoxyethyl(+)-4-[3-(5-ethoxycarbonyl-1,2,4-oxadiazol-3-yl)-phenyl]-1,4-dihydro-2,6-dimethyl-pyridine-3,5-dicarboxylate Isopropyl 2-methoxyethyl(−)-4-[3-(5-ethoxycarbonyl-1,2,4-oxadiazol-3-yl)-phenyl]-1,4-dihydro-2,6-dimethyl-pyridine-3,5-dicarboxylate Isopropyl 2-methoxyethyl, 4-dihydro-2,6-dimethyl-4-[3-(1,3,4-oxadiazol-2-yl)-phenyl] pyridine-3,5-dicarboxylate Isopropyl 2-methoxyethyl(+)-1,4-dihydro-2,6-dimethyl-4-[3-(2-methyl-1,3,4-oxadiazol-5-yl)-phenyl]-pyridine-3,5-dicarboxylate Isopropyl 2-methoxyethyl(−)-1,4-dihydro-2,6-dimethyl-4-[3-(2-methyl-1,3,4-oxadiazol-5-pyridine-3,5-dicarboxylate Isopropyl 2-propoxyethyl 1,4-dihydro-2,6-dimethyl-4-[3-(1,3,4-oxadiazol-2-yl)phenyl]-pyridine-3,5dicarboxylate.

5. A compound according to claim 1 wherein such compound is isopropyl-2-methoxyethyl-1,4-dihydro-2,6-dimethyl-4-[3-(1,3,4-oxadiazol-2-yl)phenyl]pyridine-3,5-dicarboxylate of the formula

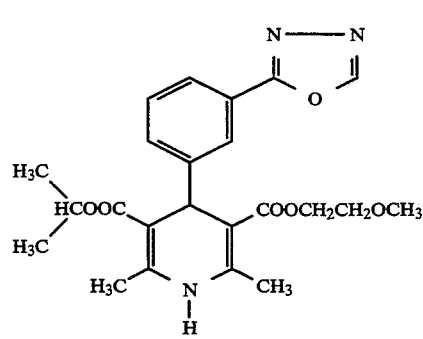

6. A compound according to claim 1 wherein such compound is isopropyl-2-methoxyethyl- 1,4-dihydro-2,6-dimethyl-4-[3-(5methyl-1,3,4-oxadiazol-2-yl)phenyl]pyridine-3,5-dicarboxylate of the formula

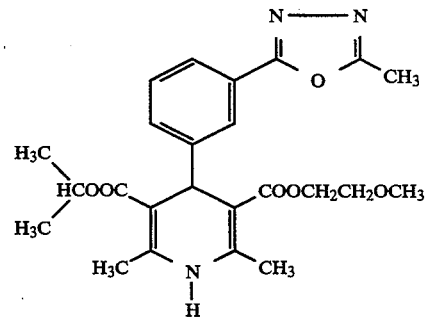

7. A compound according to claim 1 wherein such compound is isopropyl-2-methoxyethyl- 1,4-dihydro-2,6-dimethyl-4-[3-(5ethoxycarbonyl-1,3,4-oxadiazolyl-2-yl)phenyl]pyridine-3,5-dicarboxylate of the formula

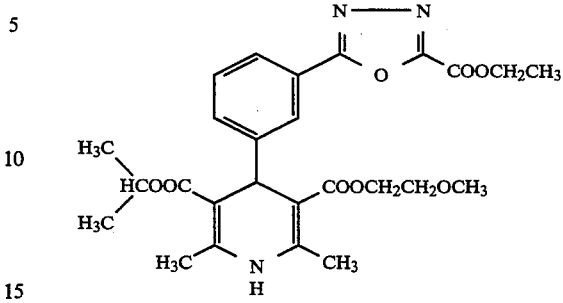

8. A composition for the treatment of diseases of the central nervous system comprising an amount effective therefor of a compound according to claim 1 and a pharmacologically acceptable diluent.

* * * * *

UNITED STATES PATENT AND TRADEMARK OFFICE
CERTIFICATE OF CORRECTION

PATENT NO. : 5,403,849
DATED : April 4, 1995
INVENTOR(S) : Schohe-Loop, et al.

It is certified that error appears in the above-indentified patent and that said Letters Patent is hereby corrected as shown below:

Col. 32, line 38    After " 2-methoxyethyl " delete " , " and substitute -- 1, --

Col. 32, line 45    Before " pyridine " insert -- yl)-phenyl]- --

Col. 32, line 47    Delete " propoxyethyl " and substitute -- methoxyethyl (-)- --

Col. 32, lines 48-49    After " 5 " insert -- - --, after "dicarboxylate " insert -- Isopropyl 2-methoxyethyl (+)-1,4-dihydro-2,6-dimethyl-4-[3-(1,3,4-oxadiazol-2-yl)-phenyl]pyridine-3,5-dicarboxylate and Isopropyl 2-propoxyethyl 1,4-dihydro-2,6-dimethyl-4-[3-(1,3,4-oxadiazol-2-yl)phenyl]=pyridine-3,5-dicarboxylate --

Signed and Sealed this

Fourth Day of July, 1995

Attest:

BRUCE LEHMAN

Attesting Officer    Commissioner of Patents and Trademarks